United States Patent [19]

Trainer et al.

[11] Patent Number: 5,094,532
[45] Date of Patent: Mar. 10, 1992

[54] METHOD AND APPARATUS FOR MEASURING SMALL PARTICLE SIZE DISTRIBUTION

[75] Inventors: Michael N. Trainer, Telford, Pa.; William L. Wilcock, Gwynedd, United Kingdom; Brian M. Ence, Lansdale, Pa.

[73] Assignee: General Signal Corporation, Stamford, Conn.

[21] Appl. No.: 432,710

[22] Filed: Nov. 7, 1989

[51] Int. Cl.⁵ .................. G01N 15/02; G01N 15/06
[52] U.S. Cl. .................. 356/336; 356/338; 356/342; 250/574
[58] Field of Search ............... 356/335-343, 356/73.1; 250/564, 565, 574

[56] References Cited

U.S. PATENT DOCUMENTS

| | | | |
|---|---|---|---|
| 3,873,206 | 3/1975 | Wilcock | 356/336 |
| 4,052,600 | 10/1977 | Wertheimer | |
| 4,134,679 | 1/1979 | Wertheimer | 356/336 |
| 4,299,489 | 11/1981 | Thery et al. | 356/336 |
| 4,637,716 | 1/1987 | Auweter et al. | 356/337 |
| 4,768,879 | 9/1988 | Melachlan et al. | 356/335 |
| 4,779,003 | 10/1988 | Tatsuno | 356/336 |
| 4,818,071 | 4/1989 | Dyott | 356/337 |
| 4,828,388 | 5/1989 | Namba | 356/339 |
| 4,890,920 | 1/1990 | Niziolek et al. | 356/336 |

Primary Examiner—Richard A. Rosenberger
Assistant Examiner—Hoa Pham
Attorney, Agent, or Firm—Harold Huberfeld

[57] ABSTRACT

A method of measuring the size distribution of moving particles within a scattering medium includes a step of directing a beam of light into the scattering medium. The frequency of the scattered light is compared to nonscattered light emitted from the scattering medium and results in the generation of a first signal having a magnitude which is indicative of the difference in frequency between the scattered light and the nonscattered light. A second signal is generated having a magnitude which varies with frequency on a linear scale. The frequency scale of the second signal is then translated to a logarithmic scale. Finally, the translated second signal is deconvolved to determine the size and distribution of moving particles within the scattering medium.

18 Claims, 5 Drawing Sheets

METHOD AND APPARATUS FOR MEASURING SMALL PARTICLE SIZE DISTRIBUTION

BACKGROUND OF THE INVENTION

The present invention relates generally to the field of measuring the size distribution of particles and more particularly to a method and apparatus for measuring the size distribution of very small particles.

In the past, a number of methods have existed for determining the size distribution of particulate material for particles in the approximate size range of 0.1 to 100 microns in diameter. For U.S. Pat. No. 3,873,206 to William Leslie Wilcock, example, issued Mar. 25, 1975, and U.S. Pat. No. 4,134,679 to Allen L. Wertheimer, issued Jan. 16, 1979, both assigned to the assignee of the present invention, describe such methods. In addition dynamic scattering instruments are capable of determining the size of particles by measuring their Brownian motion. Brownian motion is caused by random collisions between the particle and thermally excited molecules of the dispersing media. The velocity and direction of the motion is random, however the velocity distribution of many particles averaged over a long time will approach a known functional form. Since small particles are known to move faster than larger particles, the particle size can be determined by measuring this size dependent velocity distribution. For example, fiber optic doppler anemometers such as those disclosed in U.S. Pat. No. 4,637,716, to Auweter et al, patented Jan. 20, 1987, and U.S. Pat. No. 4,818,071 to Dyott, patented Apr. 4, 1989, are capable of measuring the size of very small particles down to a diameter of approximately 0.005 microns in diameter. However, such fiber optic doppler anemometers have been useful for measuring particle size accurately only when all particles are of a uniform size. Heretofore, there has been no known method of accurately measuring the particle size and distribution of very small particles of multiple sizes.

SUMMARY OF THE INVENTION

Accordingly, a method of measuring the size distribution of moving particles within a scattering medium is provided which includes a method of measuring the size distribution of moving particles within a scattering medium includes a step of directing a beam of light into the scattering medium. The frequency of the scattered light is compared to nonscattered light emitted from the scattering medium and results in the generation of a first signal having a magnitude which varies with time and is indicative of the difference in frequency between the scattered light and the nonscattered light. A second signal is generated having a magnitude which varies with frequency on a linear scale. The frequency scale of the second signal is then transmitted to a logarithmic scale. Finally, the translated second signal is deconvolved to determine the size distribution of moving particles within the scattering medium.

OBJECTS OF THE INVENTION

Accordingly, an object of the present invention is the provision of a method and apparatus for accurately measuring the size distribution of particles as small as 0.005 microns in diameter.

Another object of the present invention is the provision of a method for measuring the size distribution of small particles which can be utilized to supplement known particle size data collection techniques.

A further object of the present invention is the provision of a method for measuring the size distribution of particles having an efficient data handling technique.

Other objects, advantages and novel features of the present invention will become apparent from the following detailed description of the invention when considered in conjunction with the accompanying drawings.

DESCRIPTION OF THE PREFERRED EMBODIMENT

Figure 1:
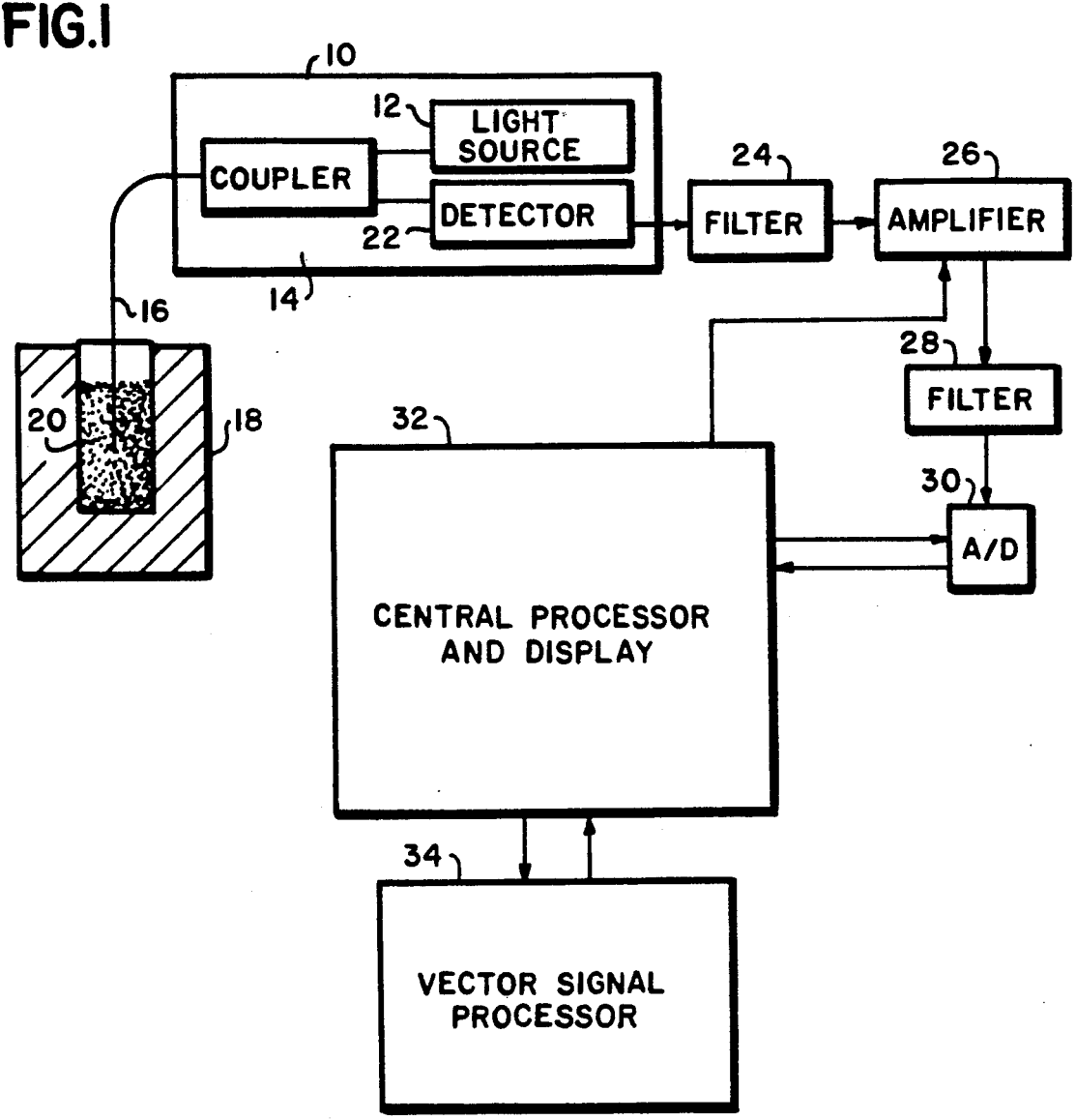
FIG. 1 shows in block diagram form an apparatus for practicing the particle size and distribution measurement of the present invention.

It should be understood that the method of measuring the size distribution of moving particles of the present invention is applicable to both light scattering instruments of the type referred to in U.S. Pat. Nos. 3,873,206 and 4,134,679 and also to dynamic scattering instruments of the type illustrated in U.S. Pat. Nos. 4,637,716 and 4,818,071 or any scattering instruments which detect Brownian motion. Referring to FIG. 1, the apparatus of the present invention will be described in connection with its use with a dynamic scattering instrument 10. The instrument 10 is preferably an optical doppler anemometer and includes a laser diode light source 12 which transmits a beam of light into an optical coupler 14. Light from the coupler 14 is transmitted along an optical cable 16, the end of which is submerged in a sample cell 18 holding particulate matter 20 suspended in a scattering medium, such as water. The particular scattering medium may be selected from a wide range of media as long as it is inert with respect to the particulate matter suspended therein.

The size distribution of the particulate matter 20 is determined by measuring the Brownian motion. As used herein, the term "size distribution" includes number, volume and area distribution.

Median velocities for typical particles between 0.005 and 2 microns in diameter is on the order of 6000 to 15 microns per second. Such velocities change direction and amplitude continuously, resulting in very small cumulative motion. Light scattering has proven to be the best method to measure such small motions. Light scattered from each particle is doppler shifted by the particle motion. These doppler frequency shifts, ranging from a few Hz to several kHz are proportional to the instantaneous particle velocity. Using frequency beating techniques it is known that one can measure such small frequency shifts which are 12 orders of magnitude smaller than the optical frequency itself.

Typically, the optical cable 16 is an optical fiber. Light emitted from the immersed end of the fiber is scattered back by th particles 20 into the fiber 16. In addition, due to the refractive index difference between the glass in the fiber core and the scattering medium, a small portion of the light emitted from the fiber is also Fresnel reflected back into the fiber. The Fresnel reflected signal has the optical frequency of the laser diode source 12 and is compared to the frequency of the scattered light from the particles 20. This comparison is made possible since the scattered light is doppler frequency shifted from the source frequency by the Brownian Motion of the particles 20. The scattered and non-scattered (Fresnel reflected) signals are back through the fiber 16 and the coupler 14 to a photodiode detector and amplifier 22.

The detector 22 generates a signal the magnitude of which varies with time and is indicative of the difference in frequency between the scattered light and the nonscattered light. This is accomplished since the detector 22 has a quadratic response which mixes (homodynes) the shifted and nonshifted light signals in a nonlinear fashion thus creating a beat frequency equal to the doppler shift of these two signals. The output signal from detector 22 is transmitted to a direct current blocking filter 24 to remove the direct current component of the signal that is introduced by the detector 22. The output from filter 24 is amplified by a low noise amplifier 26 having a gain which is selectable. The output of amplifier 26 is connected to a filter 28 whose output is in turn connected to an analog to digital converter 30. The filter 28 is preferably a 20 kHz active filter which serves as an anti-aliasing filter for the analog to digital converter 30. The filter 28 serves to remove all frequency components of the signal which are above ½ the sampling rate. It has been found that if such components are not removed they introduce an error into the end result by appearing to the system to be signals within the frequency range of interest. The analog to digital converter 30 converts the analog signal amplified at amplifier 26 and filtered in filter 28 into a format that can be easily processed by computer. The analog to digital converter 30 preferably operates at a sampling rate of 50 kHz.

The analog to digital converter 30 is connected to a central processor 32. The central processor 32 is preferably an IBM compatible personal computer. Also connected to the central processor 32 is a vector signal processor 34 preferably of the type manufactured by Burr-Brown under Model No.ZPB32-H5. The signal processor 34 generates a signal which represents the power spectrum of the signal delivered to the computer 32 by the analog t digital o converter 30. In addition, as will be discussed further herein in a particularly novel aspect of the present invention, the vector signal processor translates the linear frequency scale of the power spectrum to a logarithmic scale. The translated signal is then communicated to the central processor 32. As will be further discussed herein the central processor 32 then deconvolves the translated signal in an iterative manner to determine the size distribution of moving particles within the scattering medium. The central processor 32 also includes a display and serves to gather data from the analog to digital converter 30, control the vector signal processor 34 and display the size distribution.

Figure 2A:
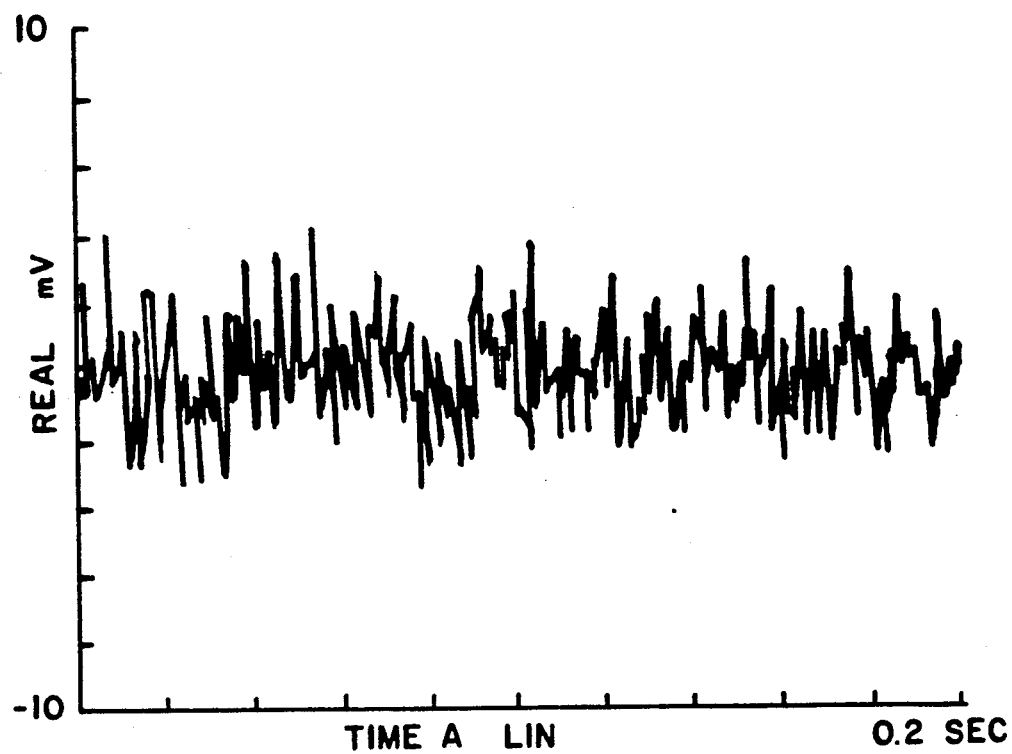
FIGS. 2A-2E show in graph form the performance of the present invention.
Figure 2B:
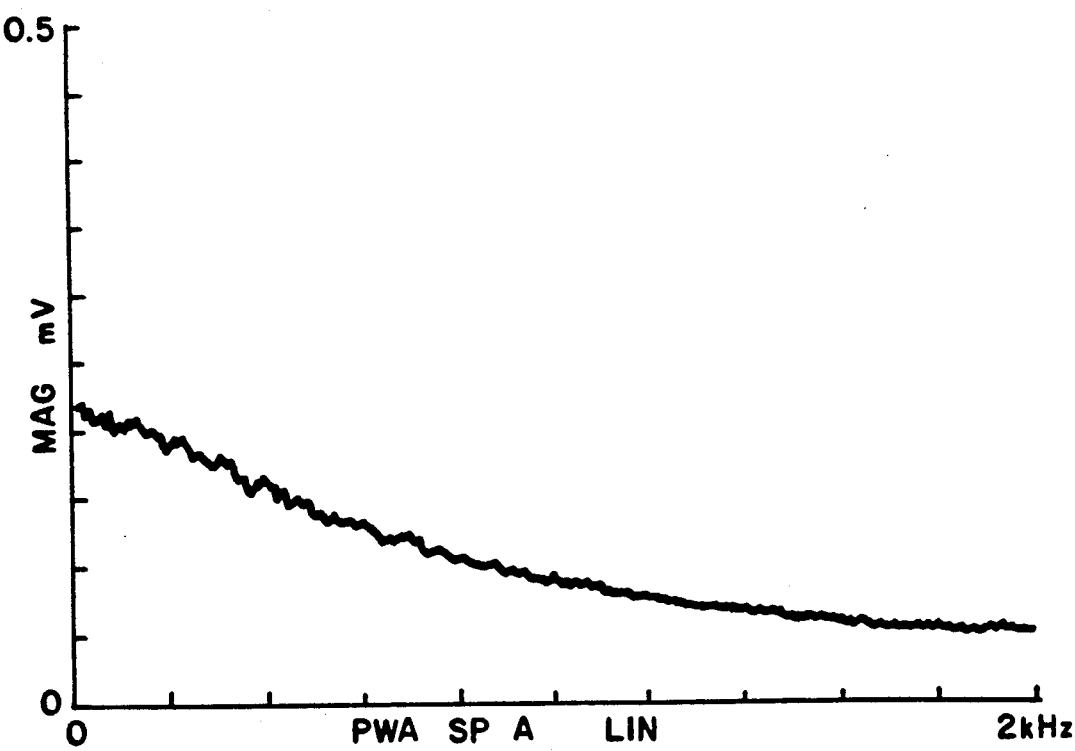

FIG. 2A shows a typical plot of voltage vs. time for a doppler beat signal from detector 22. FIG. 2B shows the square root of the power spectrum in FIG. 2A which is a plot of voltage vs. frequency. Applicants have recognized that there are many physical problems in which a function f(x) of a variable x, which can be measured, is related to function g(y) of another variable y, which it is desired to know, by an integral equation of the form $$f(x) = \int g(y)k(x,y)dy \quad (1)$$

where f measured, g is the desired unknown, and K, called the kernel of the equation, is a known function of both x and y. In general the inversion of equation (1) to obtain g from f is a non-linear problem which is complicated and may be impracticable because of measurement errors. However, if the kernel happens to be a function of the product xy, the transformation to new variables $u = \log x, 1/v = \log y$ allows (1) to be written in the form $$\bar{f}(u) = \int \bar{g}(v)\bar{k}(u-v)dv \quad (2)$$

This is a convolution integral which it is well known can be easily inverted by linear methods. An obvious extension applies to the case when K is a function of the quotient x/y, in which case the appropriate transformation is $v = \log y$.

Applicants discovered that this general principle can be applied to the problem of measuring particle size distribution since the curve illustrated in FIG. 2B can generally be defined by the particle number integral as shown by the following equations where $P_l(w)$ represents the beat signal power spectral density integrated over equally spaced frequency intervals (a linear frequency scale):

$$P_l(\omega) = \int_0^\infty \frac{2aS(a)n(a)}{\alpha\left[1 + \left(\frac{\omega a}{\alpha}\right)^2\right]} da \quad (3)$$

$$\alpha = \frac{8\pi kT}{3\lambda^2 \eta} = a\omega_0 \quad (4)$$

where
w = angular frequency
S(a) = scattering efficiency function
a = the particle radius $\omega_0 = \frac{8\pi KT}{3\lambda^2 \eta a}$ = the half power point of the Lorentzian function.

T = temperature in degrees Kelvin
K = Boltzmann's constant
λ = light wavelength
η = vicosity of the scattering medium
n(a) = the number distribution of particles per unit size interval.

Figure 2C:
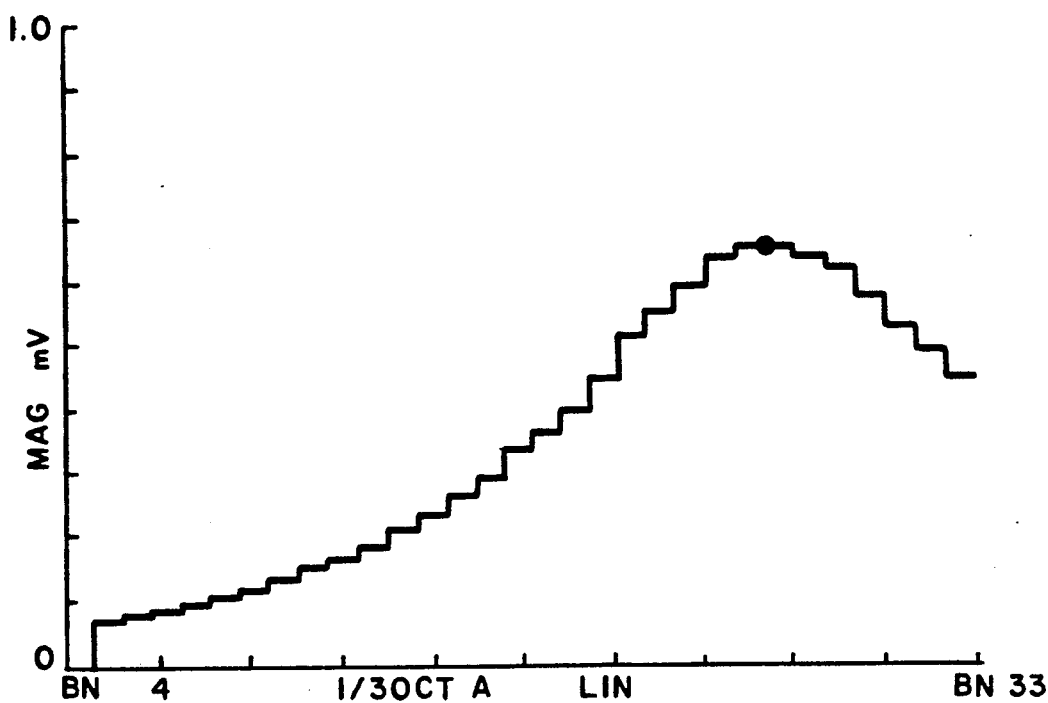

The integral equation (3) as noted above is very difficult to solve for n(a). However, as further noted above, applicants have noted that if the power spectrum is translated into logarithmic frequency space the resultant equations describe a linear shift invariant system. This type of system then allows the use of conventional deconvolution techniques to solve n(a). In order to perform the above logarithmic translation it was first determined that the logarithmic or octave based power spectrum $P_m(x)$ for a monosized particle sample is described by the following equation:

$$P_m(x) = h(x - x_a) = \frac{Zae^{(x-x_a)}}{a^2 + e^{z(x-x_a)}} \quad (5)$$

where
$x = \ln\omega$ = the logarithmic frequency variable
$x_a = -\ln a$ = the logarithmic size parameter In logarithmic space this equation is shift invariant. As to particle size (x) changes, the power spectrum simply shifts along the logarithmic frequency axis without changing shape. FIG. 2C shows a plot of voltage vs. frequency with the frequency scale translated to a ⅓ octave spectrum.

Thus the monosize power spectrum is identified as the impulse response h for a system which transforms particle size distribution to power spectrum. The following equation shows the weighted integral for a broad polysize sample in terms of the impulse response where P(x) represents the integral of the power spectral density over logarithmically progressing frequency intervals.

$$P(x) = \int N(x_a) h(x - x_a) dx_a \qquad (6)$$
$$= N(x)*h(x)$$
$$= \text{the convolution of } h \text{ and } N$$

N(x) is the product of the particle number distribution and S(x)—the scattering efficiency of the particle.

A polysize sample will produce a broad smeared power spectrum, which shows little information about the particle size distribution. However, knowing the shape of the impulse response enables one to determine the particle size distribution from the broad power spectrum. This process is called deconvolution.

It has been found that due to the large width of the power spectrum impulse response, it is difficult to deconvolve the response with conventional Fourier transform or inverse matrix techniques. The inversion of the power spectrum to particle size distribution is very sensitive to small errors (noise) in the power spectrum. But it has also been found that by using iterative deconvolution techniques one is able to determine the particle size distribution.

Such an iterative deconvolution process is outlined by the following equation set. The process is started by letting the particle size distribution be equal to some arbitrary starting function. A good starting function has been found to be the power spectrum because its shape will be similar to that of the actual particle size distribution. However, a flat distribution would also be satisfactory.

$$N_1(x) = P(x) \text{ START} \qquad (7)$$

STEP 1. $N_2(x) = K[P(x) - N_1(x)*h(x)] + N_1(x)$
STEP 2. $N_1(x) = N_2(x)$
STEP 3. Loop Back to Step 1

Then the power spectrum for this starting particle size distribution is calculated by convolution of the size distribution and the impulse response. The first approximation of the power spectrum is subtracted from the actual power spectrum, producing a function which approximates the difference between N1 and the actual particle size distribution. The difference function (multiplied by a constant K) is added to N1 to obtain a corrected distribution N2. This procedure is repeated many times; and each iteration produces a new N2 distribution which more closely agrees with the actual particle size distribution of the sample. K is the gain of this iteration process; as K is increased, larger changes in N2 are made with each iteration. This has been found to usually force the process to converge to a final result faster. However, this process is analogous to feedback in an amplifier. If the feedback gain, K, is too large, the iteration process will go into oscillation or grow exponentially, never converging to the proper distribution.

This process works well on perfect computer generated data. But, it has been found that real power spectra contain random errors due to the finite measurement time The power spectrum is calculated from a cumulation of Fourier transforms; each transform is created from the digital sampling of the detector 22 outpu signal over a period. The standard deviation of the Fourier transform data will decrease as more transforms are averaged, but total measurement time constraints limit the accuracy to be gained by averaging many transforms. The magnitude of random errors in the power spectra will decrease as the measurement time increases.

Spurious peaks can be reduced by appropriate smoothing of the input power spectrum. Only a small portion of the additive noise has broad enough features to be caused by Brownian motion. The impulse response is the sharpest feature which can be created. So the noise can be preferentially reduced by smoothing the power spectrum. The power spectrum and the impulse response must be smoothed by convolution with a smoothing function C(x) and then iteratively deconvolved as shown in the following equation In this way, the smoothing is corrected for in the deconvolution process by the use of a smoothed impulse response.

$$N_1(x) = P(x)*C(x) \qquad (8)$$

1. $N_2(x) = K[P(x)*C(x) - h(x)*C(x)*N_1(x)] + N_1(x)$
2. $N_1(x) = N_2(x)$
3. Loop Back to 1.

Figure 2D:
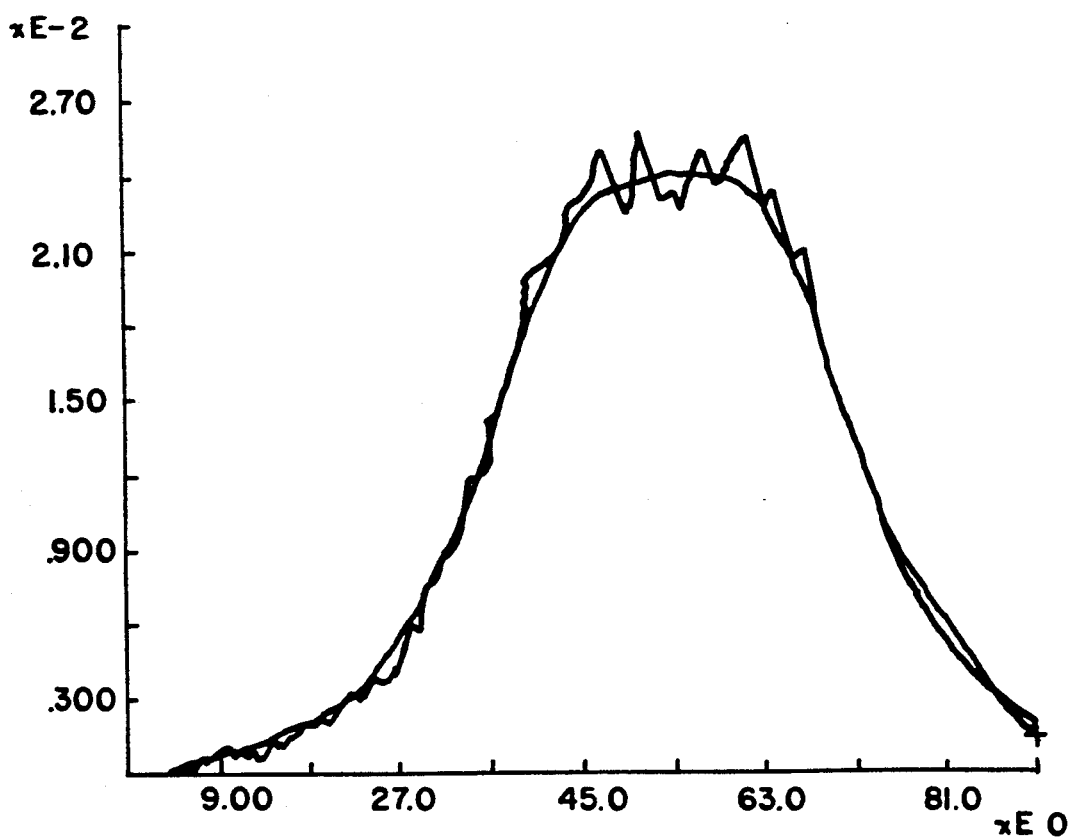
Figure 2E:
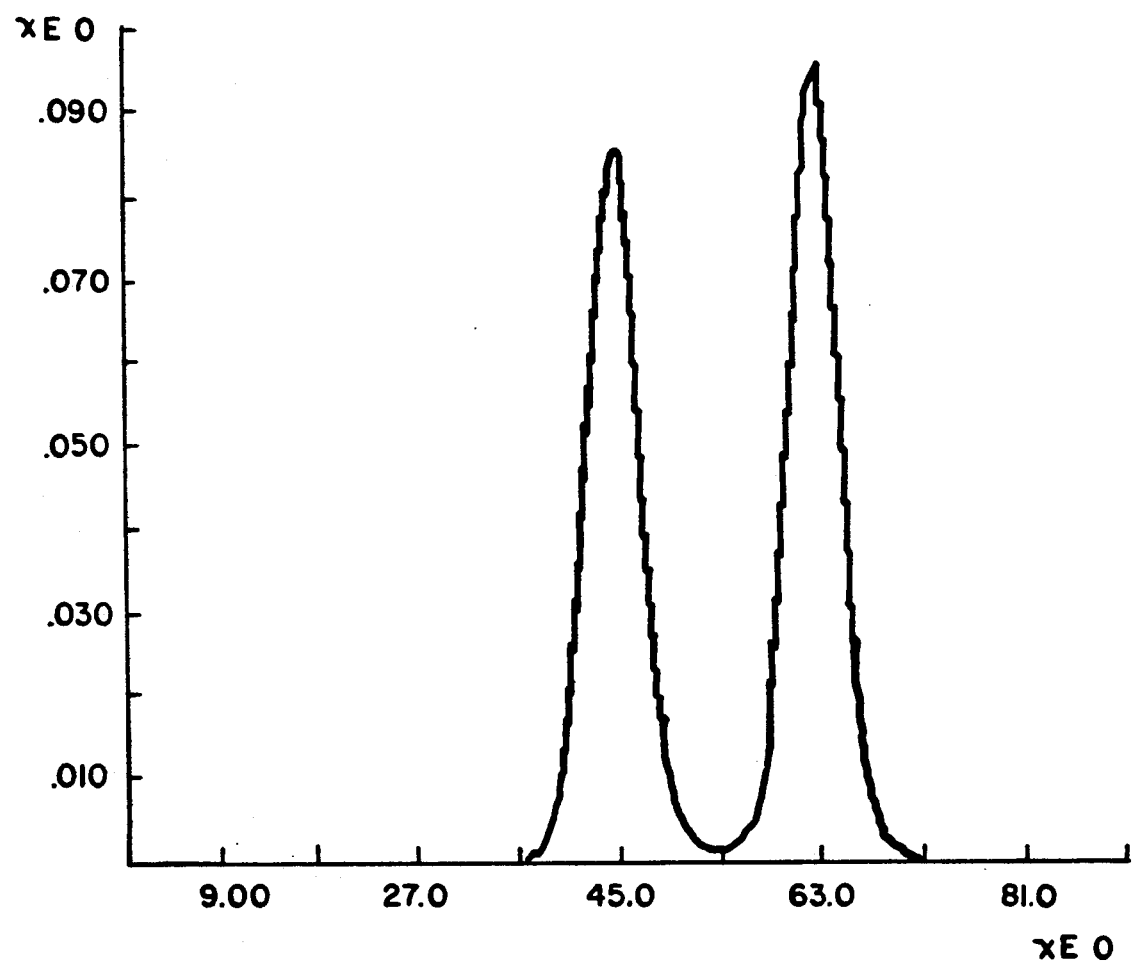

FIG. 2D shows the noisy P(x) curve and the smoothed P(x)*C(x). FIG. 2E shows the size distribution resulting from iterative deconvolution of the smoothed data. The deconvolved particle size distribution now contains only two peaks at channels 45 and 63. Any spurious peaks are eliminated.

Figure 3:
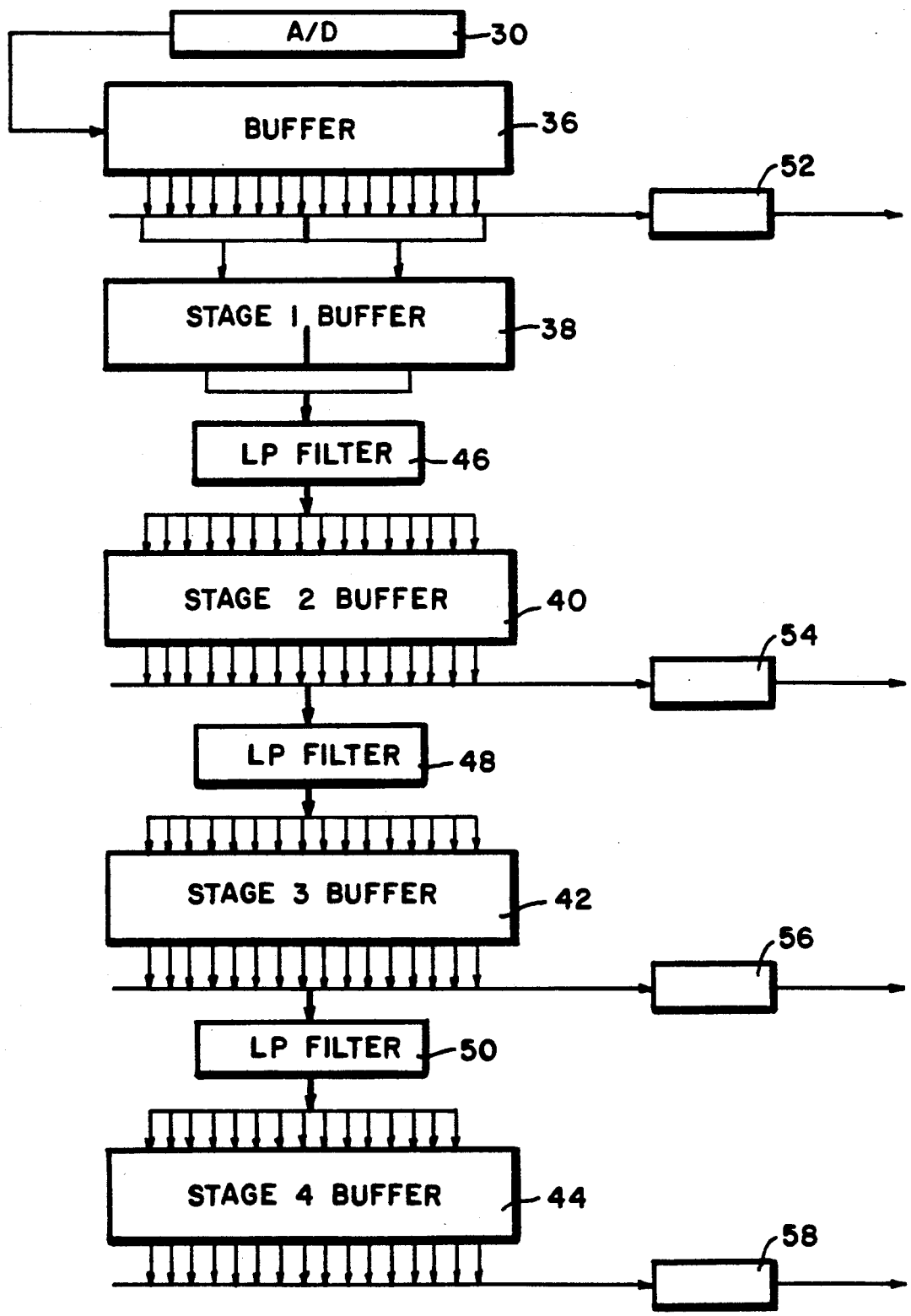
FIG. 3 shows in block diagram form a data collection and processing circuit utilized in the method of the present invention.

In connection with FIG. 3, a continuous sampling of data acquisition for the method of the present invention will be described. The analog to digital converter 30 has the capability of entering data into central processor 32 by using direct memory access. This method of data entry leaves the processor 32 free to perform other functions while the analog to digital converter 30 is operating. Data is continuously entered into a buffer 36, an area in the computer memory sufficient to hold 32K bits of data. When the buffer 36 is full, new data is placed into the buffer at its beginning overwriting the old data. The processor 32 monitors the progress of this direct memory access activity in the input buffer 36 and transfers or processes data as needed and as time permits. The data flow of the present invention serves to pass digital signals through a plurality of serially connected buffers in low pass filter stages to thereby segment the signal. Buffer 36 is serially connected to 4 buffers 38, 40, 42, and 44, separated serially by low pass filters 46, 48, and 50 respectively. Each low pass filter receives input data in the form of 32K points, filters the input data and resamples the output to create 2K points at 1/16 of the sample rate of the input data. The basic flow of data is such that as data is entered into a buffer for a given stage, it is processed to produce spectral data for that stage. When a buffer is filled, its contents are processed in the low pass filter and the output accumulated in the buffer of the next stage. In the case of the transfer of data from the direct memory access buffer 36 to the stage 1 buffer 38 half of the buffer 36 is preferably transferred at a time. The output from each stage is functionally connected to power spectrum density analyzers, 52, 54, 56 and 58 respectively. Each power spectrum density analyzer serves to receive an input of 2K points and generates 24 1/6 octave bands of power spectrum density as will be described hereinafter.

Thus, the sequence of data flow operations may be summarized:
1. Data is transferred from the lower half of the direct memory access buffer to buffer 38.
2. Data is transferred from the upper half of the direct memory access buffer to the buffer 36, data is filtered by the filter 46 and passed to buffer 40.
3. Data from buffer 40 is filtered in filter 48 and passed to buffer 42. Data from buffer 43 is filtered in filter 50 and passed to buffer 44.
4. Power spectrum density analysis is performed in power spectrum density analyzer 56.
5. Power spectrum density analysis is performed in power spectrum density analyzer 54.
6. Power spectrum analysis is performed in power spectrum density analyzer 52.
7. Power spectrum density analysis is performed in power spectrum density analyzer 58 at the completion of the data acquisition process.

The preferred sampling period is 3 minutes. The 1/6 octave bands are formed by means of fast Fourier transfer techniques (FFT).

The 1/6 octave bands are formed from the FFT analyzer outputs by summing groups of FFT channels. However, the desired edges of the 1/6 octave bands will rarely coincide with the FFT channel frequencies. Hence it has been found necessary to interpolate between the channels in order to correctly form the bands. This interpolation is done as follows.

The signal amplitude as a function of frequency for the frequency interval between FFT channels i to i+1 can be expressed by linear approximation as:

$$G(x) = F(i) + x[F(i+1) - F(i)] \quad (9)$$

where G is the signal amplitude, F(i)( is the amplitude in the ith FFT channel and x is a dimensionless variable that ranges from 0 to 1.

It is desired to find the area under the amplitude versus frequency curve between the 1/6 octave band edges. This can be done by integrating the linear approximation formula between each FFT channel over the region of interest.

To do this integration one must first divide the band edges by the FFT channel separation. The integer portion of this division will be the FFT channel just below the band edge. The fractional part will be the fractional distance of the band edge between the channels (x in the linear approximation formula). The lower band edge is expressed as i.u and the upper edge as j.v. Here i and j are the FFT channel numbers and u and v the fractional portions. One must then integrate from channel to channel using the linear interpolation formula, i.e.

$$\int_a^b [F(i) + x(F(i+1) - F(i))]dx = \quad (10)$$

$$xF(i) + \tfrac{1}{2}x^2 [F(i+1) - F(i)]$$

Three cases for the limits generally exist:
$x = u$ to 1
$x = 0$ to 1
$x = 0$ to v $$\therefore P(k) = \text{power in the Kth } \tfrac{1}{6} \text{ octave band} \quad (11)$$

$$= \tfrac{1}{2}(1 - u^2)F(i) + \left(1 - \tfrac{1}{2}u^2\right) +$$

$$\sum_{m=i+2}^{j-1} F(m) +$$

$$\left(1 - \tfrac{1}{2}(1 - v)^2 F(j) + \tfrac{1}{2}F(j+1)\right)$$

The method of the present invention is particularly useful in industrial process control for controlling one or more parameters of an industrial process which at least in part is utilized to manufacture small particulate material. In such a case, a representative sample of particles manufactured in such a process is placed in the cell 18 for measurement. Following the determination of size distribution of particles as determined by the readout from processor 32, which may be either in the form of a CRT readout or a graphic printout or a table of data or any combination thereof, the parameters of the process may be adjusted to correspondly alter particle size and size distribution within the process.

Figure 4:
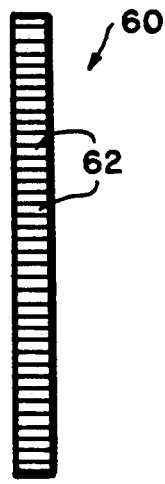
FIG. 4 shows a diagram of an alternate embodiment of the present invention

FIG. 4 shows an array 60 containing a plurality of linearly spaced photodiodes 62 which may be used in light scattering instruments of the type described in U.S. Pat. Nos. 3,873,206 and 4,134,679. Such an array measures the angle with respect to incident light at which particles being measured scatter light from a source, typically a laser source. The scattering angle then becomes the key parameter utilized to determine size distribution.

Thus, it is apparent that a method and apparatus for measuring the size distribution of moving particles within a scattering medium has been provided which is capable of measuring size distribution of particles as small as 0.0005 microns in diameter. This method can be utilized with known data collection techniques and handles data very efficiently.

While there have been described what are at the present considered to be the preferred embodiments of the present invention, it will be obvious to those skilled in the art that various changes and modifications may be made therein without departing from the invention, and it is, therefore, aimed in the appended claims to cover all such changes and modifications as fall within the true spirit and scope of the present invention.

We claim:
1. A method of measuring the size distribution of particles within a scattering medium, comprising:
   directing a beam of light into the scattering medium;
   generating a first signal the magnitude of which is indicative of a key parameter of said scattered light;
   generating a second signal by integrating a function of said first signal over equally spaced intervals of said key parameter;
   translating the integration intervals of said key parameter of said second signal to logarithmic intervals; and
   deconvolving said translated second signal to determine the size and distribution of particles within said scattering medium.

2. A method as set forth in claim 1 further including the step of creating a readout showing the size distribution of particles.

3. A method as set forth in claim 2 wherein said readout is a plot of the size distribution of particles sampled.

4. A method as set forth in claim 2 wherein said readout is in the form of a printed table.

5. A method as set forth in claim 1 wherein said translated second signal is deconvolved in an iterative manner.

6. A method as set forth in claim 1 wherein said key parameter is the angle with respect to said beam of light at which said beam of light is scattered by said particles.

7. A method as set forth in claim 6 wherein said scattered light is detected by a plurality of linearly spaced detectors.

8. A method as set forth in claim 1 further including the step of comparing said key parameter of said scattered light to non-scattered light emitted from said scattering medium and wherein said first signal is indicative of the difference in said key parameter between said scattered light and said non-scattered light.

9. A method as set forth in claim 8 wherein said key parameter is frequency, said second signal is generated by integrating the power spectral density of said first signal over equally spaced frequency intervals, and said translated second signal is generated by translating said equally spaced frequency intervals to logarithmically progressing frequency intervals.

10. A method as set forth in claim 9 wherein the step of translating said equally spaced frequency intervals to logarithmically progressing frequency intervals further includes converting said first signal from an analog to a digital signal; and passing said digital signal through a plurality of serially connected buffer and low pass filter stages to thereby segment said digital signal into a plurality of signals separated by the magnitude of the frequency they represent.

11. A method of controlling one or more parameters of an industrial process which at least in part is utilized to manufacture small particulate material, comprising:

taking a representative sample of particles manufactured in said process and placing said sample in a scattering medium;

directing a beam of light into the scattering medium;

comparing a key parameter of the scattered light to non-scattered lighte mitted from said scattering medium;

generating a first signal the magnitude of which is indicative of the difference in said key parameter between said scattered light and said non-scattered light;

generating a second signal by integrating a function of said first signal over equally spaced intervals;

translating the integration intervals of said key parameter of said second signal to logarithmic intervals;

deconvolving said translated second signal to determine the size and distribution of particles within said scattering medium and creating a readout indicative thereof;

comparing said readout to a predetermined desired particle size distribution characteristic; and adjusting the parameters of said process to correspondingly alter particle size and size distribution of said particulate material within said process.

12. An apparatus for measuring the distribution of particles within a scattering medium comprising:

a light source;

means for directing light from said source to a point within said scattering medium;

means for receiving light scattered by the moving particles within said scattering medium and generating a first signal which is indicative of a key parameter of said scattered light;

means for receiving said first signal and generating therefrom a second signal whose magnitude is the integral of a function o said first signal integrated over equally spaced intervals of said key parameter;

means for receiving said second signal and translating the integration intervals of said key parameter in said second signal to logarithmic intervals; and means for deconvolving the logarithmically translated signal and developing therefrom a readout of particle size and distribution within said scattering medium.

13. An apparatus as set forth in claim 12 wherein said means for receiving said scattered light further includes means for receiving non-scattered light from said scattering medium and means for comparing the frequency of the scattered light to the non-scattered light; wherein said first signal is indicative of the difference in frequency between said scattered light and said non-scattere light and varies with time, and wherein said particles are moving within said scattering medium.

14. An apparatus as set forth in claim 12 wherein said means for deconvolving the logarithmically translated signal is an iterative means.

15. An apparatus as set forth in claim 12 wherein said key parameter is the angle with respect to said beam of light at which said beam of light is scattered by said particles.

16. An apparatus as set forth in claim 15 wherein said scattered light is detected by a plurality of linearly spaced detectors.

17. An apparatus as set forth in claim 12 wherein said key parameter is frequency, the magnitude of said second signal is the integral of the power spectral density of said first signal integrated over equally spaced frequency intervals, and said translated second signal includes logarithmically progressing frequency intervals.

18. An apparatus as set forth in claim 17 wherien said translating means includes means for converting said second signal from an analog signal to a digital signal and means for passing said digital signal through a plurality of serially connected buffer and low pass filter stages to thereby segment said second signal into a plurality of signals separated by the magnitude of the frequency they represent.

* * * * *